(12) United States Patent
Baumann et al.

(10) Patent No.: US 8,301,236 B2
(45) Date of Patent: Oct. 30, 2012

(54) SYSTEM AND METHOD FOR HIGH RESOLUTION WIRELESS FULL DISCLOSURE ECG EPISODE MONITORING AND ANALYSIS

(75) Inventors: Eric Baumann, San Diego, CA (US);
Lev Korzinov, San Diego, CA (US);
David Bondietti, Carlsbad, CA (US);
James E. Ott, Kirkwood, MO (US)

(73) Assignee: Biomedical Systems Corporation, Maryland Heights, MO (US)

( * ) Notice: Subject to any disclaimer, the term of this patent is extended or adjusted under 35 U.S.C. 154(b) by 422 days.

(21) Appl. No.: 12/774,781

(22) Filed: May 6, 2010

(65) Prior Publication Data

US 2010/0298664 A1    Nov. 25, 2010

Related U.S. Application Data

(60) Provisional application No. 61/180,651, filed on May 22, 2009.

(51) Int. Cl.
*A61B 5/0404* (2006.01)

(52) U.S. Cl. ........... 600/523; 600/509; 607/60; 128/904

(58) Field of Classification Search ........................ None
See application file for complete search history.

(56) References Cited

U.S. PATENT DOCUMENTS

| | | | |
|---|---|---|---|
| 4,803,625 A | 2/1989 | Fu et al. | |
| 5,113,869 A | 5/1992 | Nappholz et al. | |
| 5,333,616 A * | 8/1994 | Mills et al. | 600/508 |
| 5,544,661 A | 8/1996 | Davis et al. | |
| 5,581,369 A | 12/1996 | Righter et al. | |
| 5,730,143 A | 3/1998 | Schwarzberg | |
| 5,752,976 A | 5/1998 | Duffin et al. | |
| 5,931,791 A | 8/1999 | Saltzstein et al. | |
| 5,959,529 A | 9/1999 | Kail, IV | |
| 5,966,692 A | 10/1999 | Langer et al. | |
| 6,225,901 B1 | 5/2001 | Kail, IV | |
| 6,366,871 B1 | 4/2002 | Geva | |
| 6,381,083 B1 | 4/2002 | Abarbanel et al. | |
| 6,569,095 B2 | 5/2003 | Eggers | |
| 6,664,893 B1 | 12/2003 | Eveland et al. | |
| 6,665,385 B2 | 12/2003 | Rogers et al. | |
| 6,694,177 B2 | 2/2004 | Eggers et al. | |
| 6,801,137 B2 | 10/2004 | Eggers | |
| 6,871,089 B2 | 3/2005 | Korzinov et al. | |
| 6,940,403 B2 | 9/2005 | Kail, IV | |

(Continued)

FOREIGN PATENT DOCUMENTS

AT    552780 T    4/2012

(Continued)

OTHER PUBLICATIONS

International Search Report for PCT Application No. 2010-35499 dated Jul. 26, 2010, 2 pages.

(Continued)

*Primary Examiner* — Kennedy Schaetzle
(74) *Attorney, Agent, or Firm* — Senniger Powers LLP

(57) ABSTRACT

High resolution full disclosure ECG data is transferred from a body sensor device to a handheld device via a wireless protocol. The handheld device transfers the full disclosure ECG data via a cellular network to a data center for analysis. A monitoring center communicating with the data center facilitates technician and physician review and interactions.

22 Claims, 6 Drawing Sheets

U.S. PATENT DOCUMENTS

| | | |
|---|---|---|
| 6,957,107 B2 | 10/2005 | Rogers et al. |
| 7,002,468 B2 | 2/2006 | Eveland et al. |
| 7,130,396 B2 | 10/2006 | Rogers et al. |
| 7,212,850 B2 | 5/2007 | Prystowsky et al. |
| 7,222,054 B2 | 5/2007 | Geva |
| 7,299,159 B2 | 11/2007 | Nanikashvili |
| 7,542,878 B2 | 6/2009 | Nanikashvili |
| 7,753,856 B2 | 7/2010 | Dziubinski |
| 2003/0004403 A1* | 1/2003 | Drinan et al. ............ 600/301 |
| 2004/0138575 A1 | 7/2004 | Ueyama |
| 2004/0260189 A1 | 12/2004 | Eggers et al. |
| 2005/0159667 A1 | 7/2005 | Korzinov |
| 2005/0171448 A1 | 8/2005 | Korzinov et al. |
| 2005/0182334 A1 | 8/2005 | Korzinov et al. |
| 2006/0009697 A1* | 1/2006 | Banet et al. ............ 600/485 |
| 2006/0084881 A1 | 4/2006 | Korzinov et al. |
| 2007/0015973 A1 | 1/2007 | Nanikashvili |
| 2007/0129642 A1 | 6/2007 | Korzinov |
| 2007/0130657 A1 | 6/2007 | Rogers et al. |
| 2007/0156054 A1 | 7/2007 | Korzinov et al. |
| 2007/0191723 A1 | 8/2007 | Prystowsky et al. |
| 2007/0219453 A1 | 9/2007 | Kremliovsky et al. |
| 2007/0225611 A1 | 9/2007 | Kumar et al. |
| 2007/0288067 A1 | 12/2007 | Eveland |
| 2007/0293776 A1 | 12/2007 | Korzinov et al. |
| 2008/0097231 A1 | 4/2008 | Balda et al. |
| 2008/0260173 A1 | 10/2008 | Dziubinski |
| 2009/0043360 A1* | 2/2009 | Doerr ............ 607/59 |
| 2009/0062671 A1 | 3/2009 | Brockway et al. |
| 2009/0171227 A1 | 7/2009 | Dziubinski et al. |
| 2009/0299203 A1* | 12/2009 | De Voir et al. ............ 600/509 |
| 2010/0117835 A1 | 5/2010 | Nanikashvili |
| 2010/0121157 A1* | 5/2010 | Espina et al. ............ 600/301 |
| 2011/0213620 A1 | 9/2011 | Dziubinski |

FOREIGN PATENT DOCUMENTS

| | | |
|---|---|---|
| EP | 2014235 A1 | 1/2009 |
| EP | 2030565 A1 | 3/2009 |
| WO | 2006/001005 A2 | 1/2006 |
| WO | 2006/021956 A2 | 3/2006 |
| WO | 2007/043902 A2 | 4/2007 |
| WO | 2007/083315 A2 | 7/2007 |
| WO | 2007083314 A2 | 7/2007 |
| WO | 2008/104983 A2 | 9/2008 |
| WO | 2009027812 A2 | 3/2009 |
| WO | 2011061606 A2 | 5/2011 |

OTHER PUBLICATIONS

PocketECG: The next generation mobile arrhythmia diagnostic system, http://www.medicalgorithmics.com/info/ecg, Sep. 10, 2009, 1 page.

Kunzmann, U. et al., Parameter Extraction of ECG Signals in Real-Time, Biomed Tech (Berl) (2002) 47 Suppl 1 Pt 2:875-8, 5 pages.

* cited by examiner

SYSTEM AND METHOD FOR HIGH RESOLUTION WIRELESS FULL DISCLOSURE ECG EPISODE MONITORING AND ANALYSIS

BACKGROUND

The present invention generally relates to a wireless full disclosure analysis and monitoring system and, in particular, an ECG analysis and monitoring system used for the diagnosis of cardiac arrhythmia in ambulatory patients.

Remotely monitoring ambulatory patients for arrhythmia and promptly notifying a caregiver when a serious arrhythmia has been discovered presents many challenges. ECG (electrocardiographic) signals detected by a remote monitor are subject to noise from both patient movement and environmental sources. This noise must be reduced sufficiently to allow accurate reproduction of the ECG signals and accurate analysis of any arrhythmias present in that signal. In addition, the arrhythmia analysis algorithm must operate in a resource constrained, embedded system.

In some approaches, wide area wireless communications are employed in order to allow the transmission or notification of serious arrhythmias to the caregiver while the patient is ambulatory. However, wireless transmission is expensive in terms of both power consumption and airtime charges. In addition, wide area wireless network coverage is not always available in all areas, especially in patient's homes. In order to maintain the ability to notify a caregiver of a serious arrhythmia with low latency (near-real time), an alternate communication path is often required in the patient's home.

In order to manage power consumption and airtime charges, as well as the technician time it takes to review the transmissions, some approaches have limited remote monitor transmissions to as low a rate as possible by reducing the arrhythmia algorithm sensitivity to the minimum levels needed to maintain adequate diagnostic capability. Achieving the correct balance of algorithm sensitivity to positive predictivity in order to limit the amount of data transmitted can be challenging in the presence of signal artifact and when the patient exhibits a chronic arrhythmia.

Thus, there is a need for a cost effective remote monitoring system that can provide reliable full disclosure ECG analysis and reliable arrhythmia detection and transmission of samples of serious arrhythmias quickly to a caregiver, 24 hours a day. In particular, there is a need for a cost effective remote monitoring system that can provide reliable full disclosure analysis and reliable detection and transmission of samples of serious arrhythmias quickly to a caregiver, 24 hours a day.

SUMMARY

In one form, the invention provides high resolution, full disclosure data acquired at the patient on a body worn sensor.

In another form, the invention provides high resolution, full disclosure ECG (electrocardiographic) data acquired at the patient on a body worn sensor. The full disclosure ECG data is stored and then transmitted to a handheld device using a local area wireless technology such as Bluetooth™. The handheld device stores and transmits the data via a cellular network to a data center. At the data center, all full disclosure ECG data is stored and then analyzed for arrhythmia. The full disclosure ECG data including the portions containing arrhythmic episodes are transmitted to a monitoring center for analysis and confirmation by a technician before being compiled into a report and transmitted to a physician. The system also allows for real time 2-way communications of voice and text messages between the patient and the technician or physician.

Other features will be in part apparent and in part pointed out hereinafter.

BRIEF DESCRIPTION OF THE DRAWINGS

Corresponding reference characters indicate corresponding parts throughout the drawings.

DESCRIPTION

Figure 1:
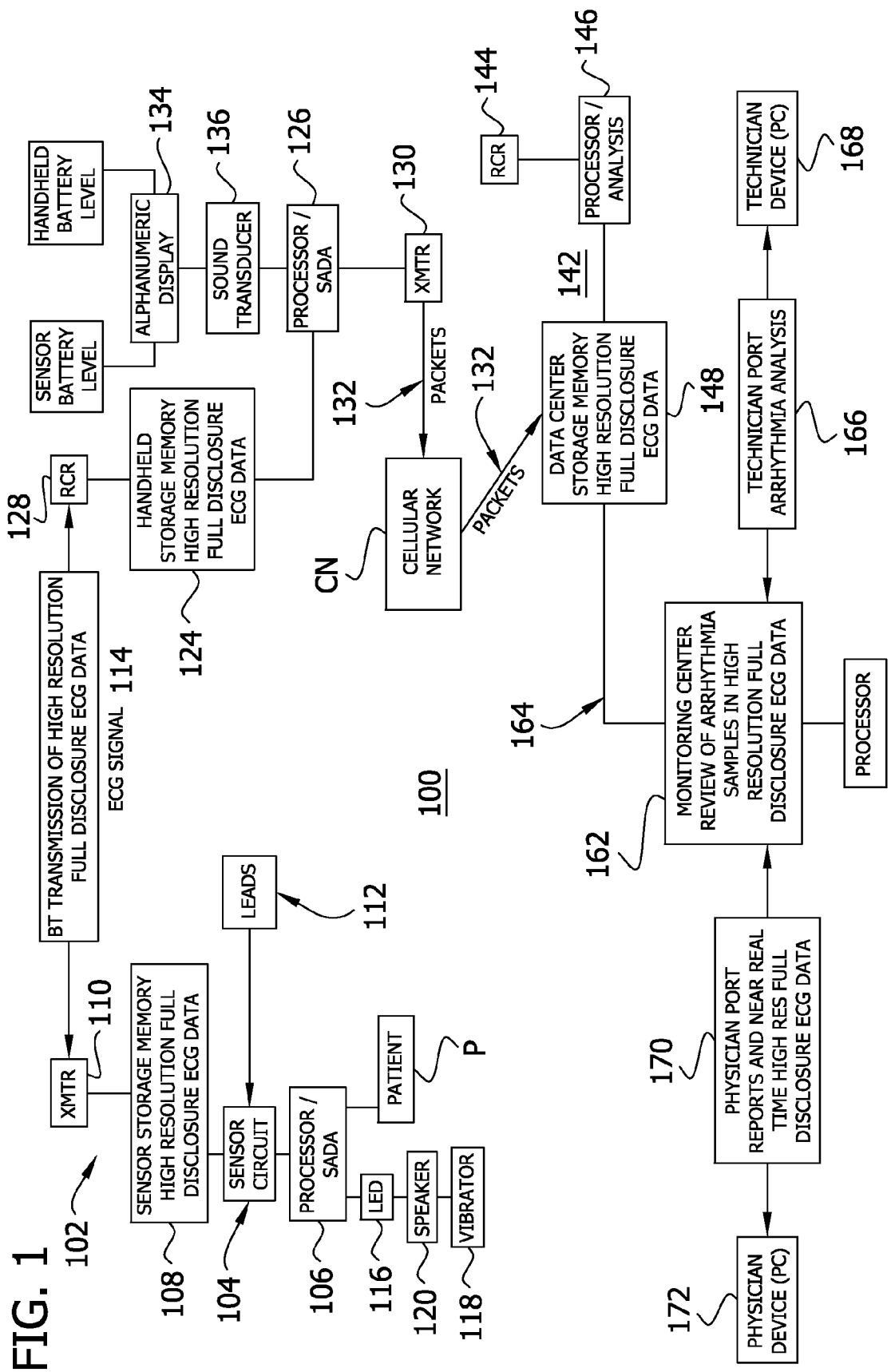
FIG. 1 is a block diagram of one embodiment of a system of the invention.

The present invention as shown in FIG. 1 is a system 100 for use by a patient P having access to a cellular network CN. A body sensor device 102 is adapted to be worn by the patient P has a sensor circuit 104, a sensor processor 106, a sensor storage memory 108 and a sensor transmitter 110. The sensor circuit 104 detects full disclosure data of the patient P, such as ECG data. In one embodiment, the sensor circuit 104 comprises leads 112 attached to the patient's skin and providing a sampled analog full disclosure ECG signal. The sensor processor 106 converts the sampled signal to full disclosure ECG data and stores the full disclosure ECG data in the sensor storage memory 108, and the sensor transmitter 110 transmits a full disclosure ECG (electrocardiographic) signal 114 including the full disclosure ECG data stored in the sensor storage memory 108. In one embodiment, the sensor device 102 is energized by one or more AAA batteries which are changed every day. The sampled full disclosure ECG signal acquired by the body sensor device 102 from the sensors 112 comprises at least 2 channels, each providing a high resolution [e.g., in the range of about 10 to 1.25 uV per bit] full disclosure ECG acquisition signal (up to 1.25 microvolts per bit, 1000 Hz 16 bit samples per second, dynamic range of +/−40 mV, 0.05 to 150 Hz bandpass). In one embodiment, the processor 106 of the body sensor device 102 incorporates a muscle artifact rejection algorithm for noise rejection. In another embodiment, the data center 142 includes a muscle artifact rejection algorithm for noise rejection.

In one embodiment of the sensor device 102 in which the sampling rate is 1000 Hz, a low-pass FIR filter is used to downsample the data. The result of this filter is divided by 32768 (e.g., bit-shift by 15). To downsample the original data, this filter is run once every 4 samples, therefore, the output frequency will be 1000/4=250 Hz.

In one embodiment, the sensor device 102 may be provided with a display such as a multicolored LED 116 driven by the processor 106. The processor 106 would be programmed to flash the LED 116 red to alert the patient of a serious event or a device malfunction, orange to indicate an alert condition and green to indicate a no-alert condition and the device is functioning properly. Alternatively or in addition, a vibrator

118 may be included with the device 120 to also alert the patient wearing the device of the event. Alternatively or in addition, a speaker 120 or other sound producing device may part of the sensor device to provide an audible alert to the patient.

A handheld device 122 is adapted to be carried by the patient P and includes a handheld storage memory 124, a handheld processor 126, a handheld receiver 128 and a handheld transmitter 130. The handheld receiver 128 receives the full disclosure ECG signal 114 from the body worn sensor device 102 and the handheld processor 126 stores the full disclosure ECG data included in the received full disclosure ECG signal in the handheld storage memory 124. Optionally, the body sensor device 102 and the handheld device 122 communicate via a low power Bluetooth (BT class 3) technology for power saving. The handheld transmitter 130 transmits a packet signal 132 including the full disclosure ECG data stored in the handheld storage memory 124 via the cellular network CN.

In one embodiment, the handheld device 122 is energized by a rechargeable battery and comprises an integrated application and baseband processor in a pre-certified cellular communications module such as a Q2687 module by Wavecomm thereby providing lower cost and lower complexity.

In one embodiment, the handheld device 122 may be provided with a display such as an alphanumeric display 134 driven by the processor 126. The processor 126 would be programmed to display text messages to the patient P on the display 134. In addition, other menu items on the display 134 may include device information, wireless settings, battery levels, volume controls, and record symptoms (by which the patient can record their symptoms at any instant in time). In one embodiment, it is contemplated that the display 134 may indicate the battery levels of both the sensor device 102 and the handheld device 122. In this embodiment, the sensor device 102 would transmit information indicating its battery level to the handheld device 122 for display.

Alternatively or in addition, a sound transducer 136 or other sound or light producing device may part of the handheld device 122 to transmit audible messages to and from the patient P. In one embodiment, the display 134 of the handheld device 122 may be driven by the processor 126 to display one or more smart keys, soft keys and/or a soft keypad which have various functions depending on the screen that is being displayed. An icon or word may appear on the screen adjacent to each smart key to identify its function. Also, the handheld device 122 may be programmed such that the processor 126 generates a low frequency single or dual tone regular/low frequency alert indicator via the sound transducer 136.

In one embodiment, it is contemplated that the sensor storage memory 108 and/or the handheld storage memory 124 each be configured to store at least 30 days of full disclosure ECG data storage. This would serve as a back up to the full disclosure ECG data in the situation where transmission of the data does not occur for some reason. For example, the sensor storage memory 108 and the handheld storage memory 124 would each be about two (2) gigabytes. Preferably, the handheld device supports at least 2 GB of nonvolatile storage for full disclosure ECG data and other files. All full disclosure ECG data will maintain the serial number of the sensor 102 from which it was acquired as well as a timestamp supplied by the sensor 102. Thus, redundant data copies are available from the data center and from the handheld device and/or the sensor device.

Each device 102, 122 may also include a flash card memory as its storage memory for storing the data and an external USB interface for remote access by a second device for such purposes as data transfer to/from the second device, and for device configuration, provisioning, and diagnostics.

A data center 142 remote from the patient P has a data center receiver 144, a data center processor 146 and a data center storage memory 148. The data center receiver 144 receives the packet signal 132 from the handheld device 122 and the data center processor 146 stores the full disclosure ECG data included in the received packet signal 132 in the data center storage memory 148. The data center processor 146 includes analysis software executed by the processor 146 to analyze the full disclosure ECG data stored in the data center storage memory 148. The software conducts waveform analysis to identify any anomalies (e.g., abnormal ECG waveforms) in the full disclosure ECG data stored in the data center storage memory 148. This configuration permits the data center 142 to process the full disclosure ECG data from multiple patients simultaneously.

In one embodiment, the data center processor 146 includes software which provides a navigable waveform or "map" that provides drill down access to portions of a particular day's full disclosure ECG data. Thus, a technician via the technician device 168 or a physician via the physician device 172 can view reports or summaries of the full disclosure ECG data and drill down to fundamental full disclosure ECG data on which to reports or summaries are based. In addition, the software may present a secondary measure such as heart rate or noise level of the full disclosure ECG data. For example, the data center processor 146 permits the technician and/or the physician to view the stored full disclosure ECG data in low resolution [e.g., 24 hours across a page] and to drill down selected full disclosure ECG data to a higher resolution [e.g., 8 seconds across a page]. The data center may permit the technician and/or the physician to view the stored full disclosure ECG data of a particular period of time and to view related ECG data to the particular period of time. For example, related data may include ECG data before or after the particular period of time and may include other parameter data during, before or after the particular period of time.

In one embodiment, the data center is configured as expandable (scalable) so that additional processors 146 may be added to handle additional sensor/handheld combinations.

A monitoring center processor 162 linked to the data center 142 by a wired or wireless network 164 provides review of the data samples of arrhythmia in high resolution full disclosure ECG data. The data samples (herein "markers" or "pointers") are portions of the high resolution full disclosure ECG data and not merely an indication of detected events. Since the processor 162 has full disclosure data available, a primary purpose of this embodiment is to identify and provide to the technician the portions of data of arrhythmias contained in the full disclosure data. Simultaneously, the technician continues to have access to all full disclosure ECG data, not just an indication of events or only the identified samples, so that the technician can scroll backward or forward from a point of view within the data to evaluate the data previous in time to the point of view or subsequent in time to the point of view. Providing markers or pointers is different from detecting events based on predefined limits and transmitting only those events (containing ECG data) to the technician because transmitting events does not allow a technician to scroll backward or forward. Thus, the processor 162 provides markers or pointers into the full disclosure ECG data for the technician to review.

The processor 162 has a technician port 166 accessible by a technician device 168 under the control of a technician. The technician uses the device 168 to view the results of the software analysis and for viewing and evaluating the full disclosure ECG data stored in the data center storage memory 148. In particular, the technician uses the device 168 to consider any anomalies identified during the processing of the full disclosure ECG data by the data center processor 146 so that the technician via the technician device 168 can provide reports relating to the technician's evaluation and/or relating to the identified anomalies. A physician port 170 accessible by a physician via a physician device 172 views the provided technician reports and may view the full disclosure ECG data stored in the data center storage memory 148. As a result, the system of FIG. 1 has the ability to telemeter full disclosure ECG data from patients at locations remote from the data center device 142, remote from the technician device 168 and remote from the physician device 172.

In one embodiment, the data center 142 includes the following software components: a communications subsystem responsible for managing two way data communications with the handheld devices 122; monitoring applications as a primary interface used by technicians for reviewing full disclosure ECG data and samples of arrhythmias contained in the full disclosure ECG data, preparing reports and managing patient and billing records; monitoring applications used by physician offices to review reports and patient records; physician facing applications as a primary web based interface used by physician offices for reviewing reports and patient clinical and billing information; an arrhythmia analysis subsystem which performs the automated arrhythmia analysis algorithms on full disclosure ECG signals received from the communications subsystem and outputs annotations to storage and arrhythmia sample markers (or pointers) to the monitoring center web applications; a reporting subsystem which generates, stores and transmits clinical and billing reports; and device management applications providing visibility to device status as well as provisioning and configuration.

The system 100 may be configured for two way communication between the patient P and the physician device 172 and/or between the patient P and the technician device 168. In one embodiment, this two way communication may be accomplished by two way communication between the handheld device 122 and the data center 142 and between the data center 142 and the monitoring center 162. In this configuration, the system 100 has the ability to transmit to the display 134 and/or the sound transducer 136 of the handheld device 122 a custom text message and/or a voice instruction to the patient P from the technician device 168 via the monitoring center 162 and/or from the physician device 172 via the monitoring center 162 to meet a particular clinical need. Also, the patient P may transmit a message from the handheld device 122 to the technician device 168 via the monitoring center 162 and/or from the physician device 172 via the monitoring center 162.

In another embodiment, this two way communication may be accomplished by two way communication between the sensor device 102 and the handheld device 122, between the handheld device 122 and the data center 142 and between the data center 142 and the monitoring center 162. In this configuration, the system 100 has the ability to transmit to the display 116 of the sensor device 102 a custom text message and/or a voice instruction to the speaker 120 or a vibration alert to the vibrator 118 from the technician device 168 via the monitoring center 162 and/or from the physician device 172 via the monitoring center 162 to alert the patient P of a particular clinical need. Optionally, the body worn sensor 102 may have a keypad or microphone so that the patient P can transmit a message from the sensor device 102 to the technician device 168 via the monitoring center 162 and/or from the physician device 172 via the monitoring center 162.

In one embodiment, near real-time streaming of the full disclosure ECG data is available for viewing by the physician or technician via the devices 168, 172. The sensor transmitter 110 streams in near real-time to the handheld transmitter 128 an ECG signal down-sampled to 125 to 250 Hz. In turn, the handheld transmitter 128 streams in near real-time to the data center receiver 144 the packet signal. The data center 142 streams ECG data included in the received packet signal 132 to the technician port 166 for near real-time viewing by the technician via the technician device 168. In addition, the data center 142 streams the ECG data included in the received packet signal 132 to the physician port 170 for near real-time viewing by the physician 172. In one embodiment, the handheld transmitter 130 transmits to the data center 142 packet signals 132 with low latency to facilitate near real-time streaming.

In one embodiment, the sensor processor 106 includes an SADA (serious arrhythmia detection algorithm) program which is executed by the processor (although it is contemplated that the handheld processor 126 may have a SADA in addition to or instead of the sensor). The SADA program analyzes ECG down-sampled to 250 Hz in near real-time to detect certain serious arrhythmias, as noted below. It is contemplated that the SADA program may be selectively executed only during periods when the handheld and cellular network CN are not communicating and/or the sensor may execute the SADA when the sensor and handheld devices are not communicating. If the SADA is operating because the handheld device is not communicating with the cell network but the sensor is communicating with the handheld device, and if conditions indicative of a serious arrhythmia are detected, the sensor may alert the patient or may send a signal to the handheld so that the handheld alerts the patient or both the sensor and handheld may alert the patient. Thus, the SADA program provides an alert to the patient when one or more serious arrhythmias are detected.

In one embodiment, the processor 126 of the handheld device 122 would selectively execute the SADA (Serious Arrhythmia Detection Algorithm) to detect serious arrhythmias. This detection would be enabled whenever the device is outside of communication range of the primary communications link, such as when the link is not present for more than three regular communication intervals. Also, the SADA may be capable of detecting ventricular fibrillation and asystole. The handheld device 122 may incorporate a lossless compression mechanism for compression of full disclosure ECG data. Alternatively or in addition, either the handheld device 122 and/or the sensor device 102 may support a lossy compression algorithm that will reduce the resolution of full disclosure ECG data in the presence of noise. This algorithm should not reduce the resolution of the data to less than 12 bits over a range of 10 mV. This renders the algorithm lossless with respect to the requirements of AAMI EC38 for type 1 devices. Also, if conditions indicative of a serious arrhythmia are detected during a period when the device is outside of communication range of the primary communications link, the alert may include an indication to the patient to more to an area within the communication range of the primary communications link or the POTS modem.

Figure 5:
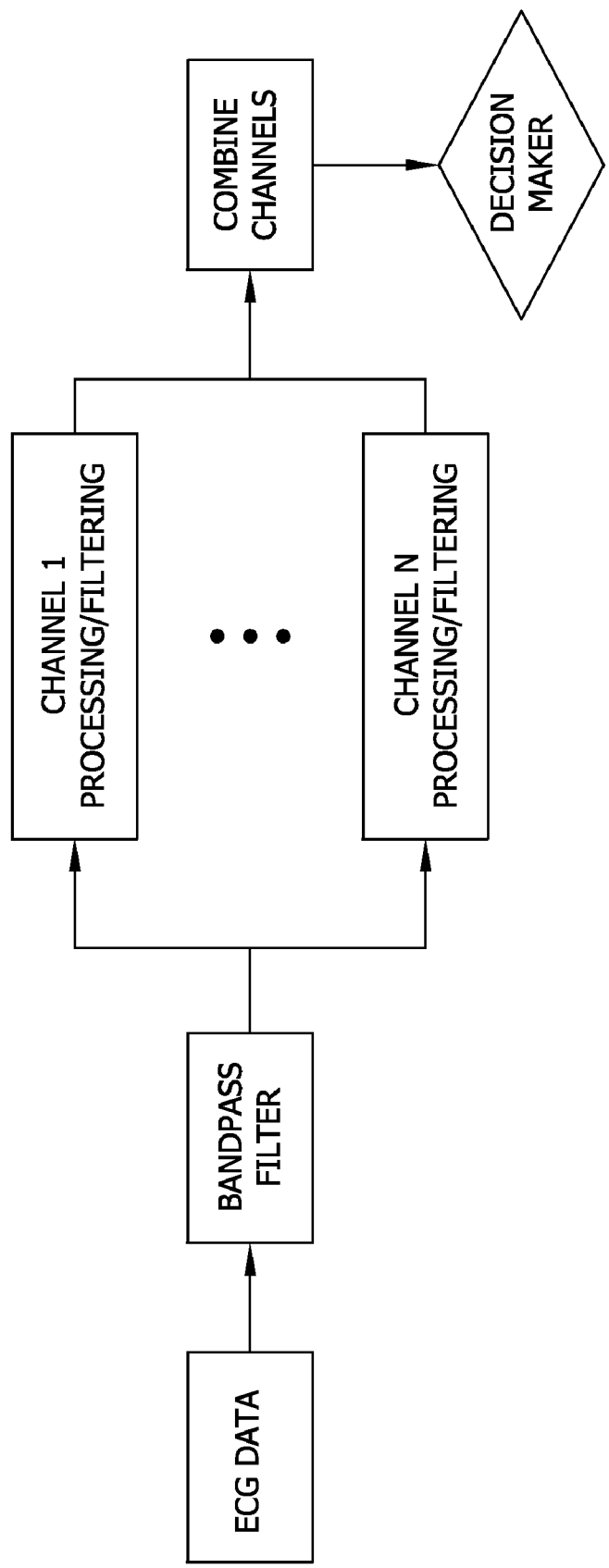
FIG. 5 illustrates a ventricular fibrillation and/or SADA algorithm.

The SADA may be implemented as illustrated in FIG. 5, executed by either the sensor processor 106 or the handheld processor 126 or both. Such SADA algorithms detect conditions indicative of serious arrhythmias such as high heart rate (e.g., ventricular tachycardia and/or ventricular fibrillation, and/or asystole). In this embodiment, the SADA algorithm estimates the ratio of slow movements of the full disclosure ECG data (ventricular repolarization and baseline) vs. fast movements of the full disclosure ECG data (R-wave). This ratio is low for a normal rhythm because most of the time the full disclosure ECG data is trending around a baseline. When the heart rate becomes higher, this ratio also increases because fast movements of the full disclosure ECG data occur more frequently as compared to slow baseline movements. The ratio is also high for ventricular fibrillation rhythms because fast movements of the full disclosure ECG data occur frequently due to fibrillating ventricles. The SADA algorithm indicates when the analyzed heart rate is close to or above 200 beats per minute (this number is an estimate because exact heart rate is not calculated). In this embodiment, the SADA algorithm includes band-pass filtering, low-pass filtering for the signal, channel combination logic and a decision maker.

In addition, the decision maker holds an alarm for 30 seconds after the above condition is changed to false. This prevents frequent retriggering of the same condition.

In one form, the alert provided by the SADA program may be any one or more of the following: providing an audible signal via the speaker 120 of the body sensor device 102, providing a visual signal via a light transducer of the body sensor device 102 such as flashing the LED 116 of the body sensor device 102, providing a message on a display (not shown) of the body sensor device 102, flashing an LED (not shown) of the handheld device 122, providing an audible signal via the sound transducer 136 of the handheld device 122, providing a visual signal via a light transducer (not shown) of the handheld device 122, and providing a message on the display 134 of the handheld device 122.

Figure 2:
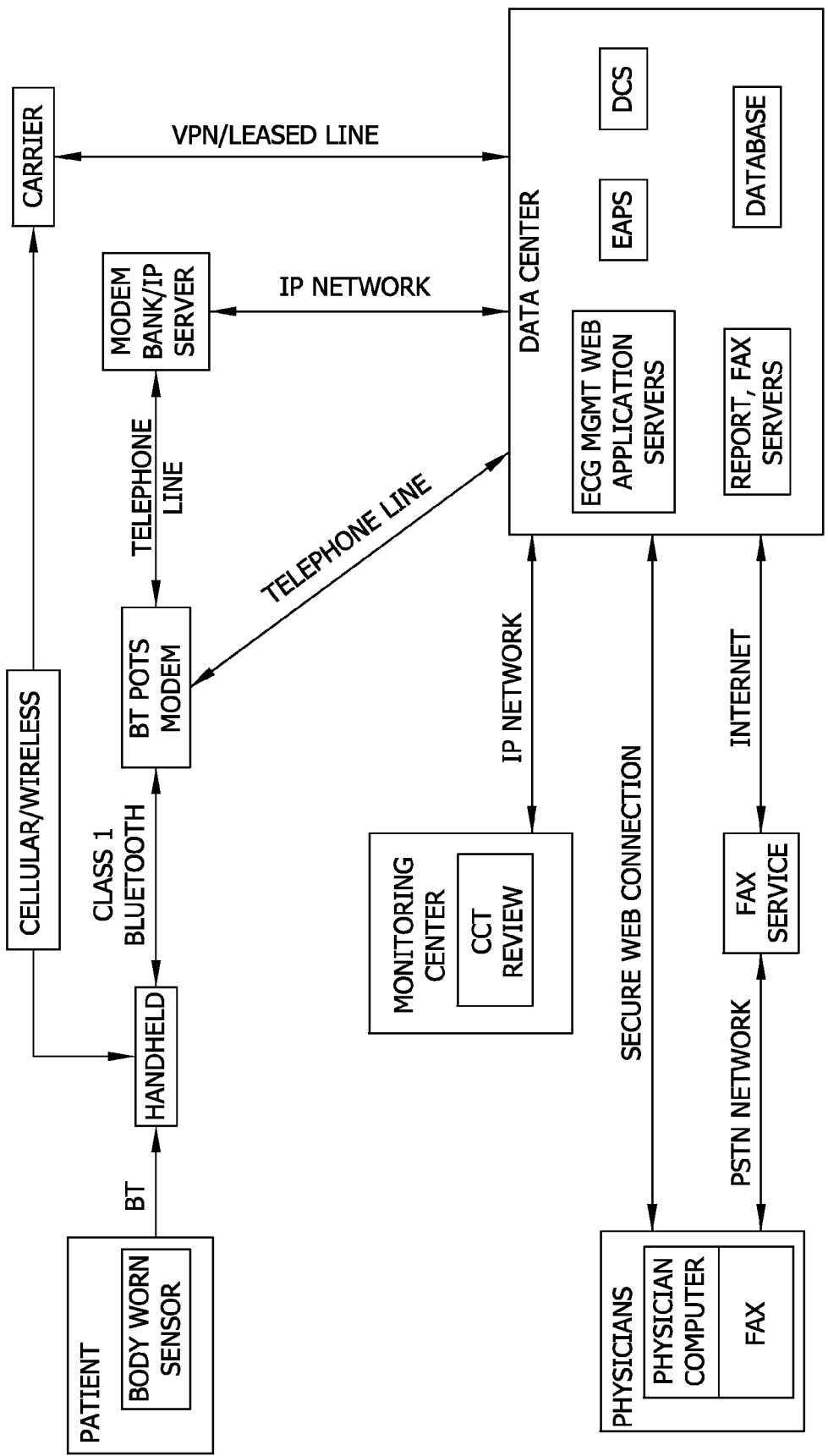
FIG. 2 is a block diagram of another embodiment of the system of the invention including a POTS modem.

In one embodiment, as shown in FIG. 2, a modem may be used as an alternative to connect the handheld device 122 to the data center 142, preferably as a back-up to the cellular network CN connection. In particular, the handheld transmitter 130 transmits a second signal including the full disclosure ECG data when the cellular network CN and handheld device are not communicating. A modem, such as a POTS modem, located at the patient's site has a receiver for receiving the second signal including the full disclosure ECG data and a transmitter for transmitting the full disclosure ECG data to the data center via a phone line, a communications network, the Internet or some other internet provider (IP) network. In one embodiment, a class 1 Bluetooth radio may be used between the handheld device and a POTS (plain old telephone system) modem for more range.

As shown in the FIG. 2 embodiment, it is contemplated that the handheld in control of the POTS modem may communicate with the data center in several ways:

1) via a circuit switched data (CSD) connection which is a direct connection between modems over the telephone line without going over the internet or using an internet protocol (IP) on an internal network. This would be a packet data protocol (not necessarily IP) over CSD; or
2) via an Internet Protocol Network (e.g., technically over a CSD connection) between the handheld using the modem and terminating at an external (to the data center) ISP, after which the signals are routed over a secure sockets protocol layer over IP to the data center. This would be packet data (using Internet Protocol) from the handheld to ISP to data center; or
3) via Internet Protocol to modems housed at the data center directly (effectively the ISP is located in the data center).

Thus, in the embodiment of FIG. 2, the ISP could be located external to the data center and use an IP to communicate with the servers in the data center via the Internet or via a dedicated circuit. Alternatively, the ISP could be located in the data center and use an IP over an internal network to transfer the data from the equipment housing the terminating modems to the DCS servers.

As shown in FIG. 2, the handheld device 122 may optionally access a WAN and includes at least one of:
   Graduated back off and PDP [Packet Data Protocol] context re-connect algorithms;
   Use of adaptive ECG resolution to reduce data payload;
   Use of lossless compression to reduce data payload; and
   Ability to connect to a home based POTS modem with a class 1 BT Radio incorporated in the handheld.

Referring to FIG. 2, this embodiment illustrates a low power RF communication, such as class 3 Bluetooth, between the body worn sensor and the handheld device as compared to a higher power RF communication, such as class 1 Bluetooth, between the handheld device and the BT POTS modem linking the handheld to the data center via a telephone line. The packet communication between the handheld device and the data center is established via cellular or other wireless network via a carrier link to the data center via a VPN/leased line.

As illustrated, the data center would include a device communication service (DCS) for receiving and storing the packets of ECG data in a database, an EAPS (ECG Analysis and Processing Subsystem; see FIG. 3) for processing the ECG data, report and fax servers for providing reports and faxes to the physician, technician and/or patient. In other words, the DCS is the subsystem responsible for communications with the devices in the field. EAPS performs the algorithm processing and ECG management web application servers provides the database and user interface. Additional servers can optionally be added to scale the application to support more users.

The results of the ECG data processed by the data center are available in several different ways. The data center may be linked to the monitoring center by an IP network so that a certified cardiac technician (CCT) may access the raw or processed data and reports. In addition, the data center may be linked to a physician device (computer) by a secure web connection so that the physician may access the raw or processed data and reports. In addition, the report and fax servers may be linked by the Internet to a fax service for providing faxes over the public switched telephone network (PSTN).

Figure 3:
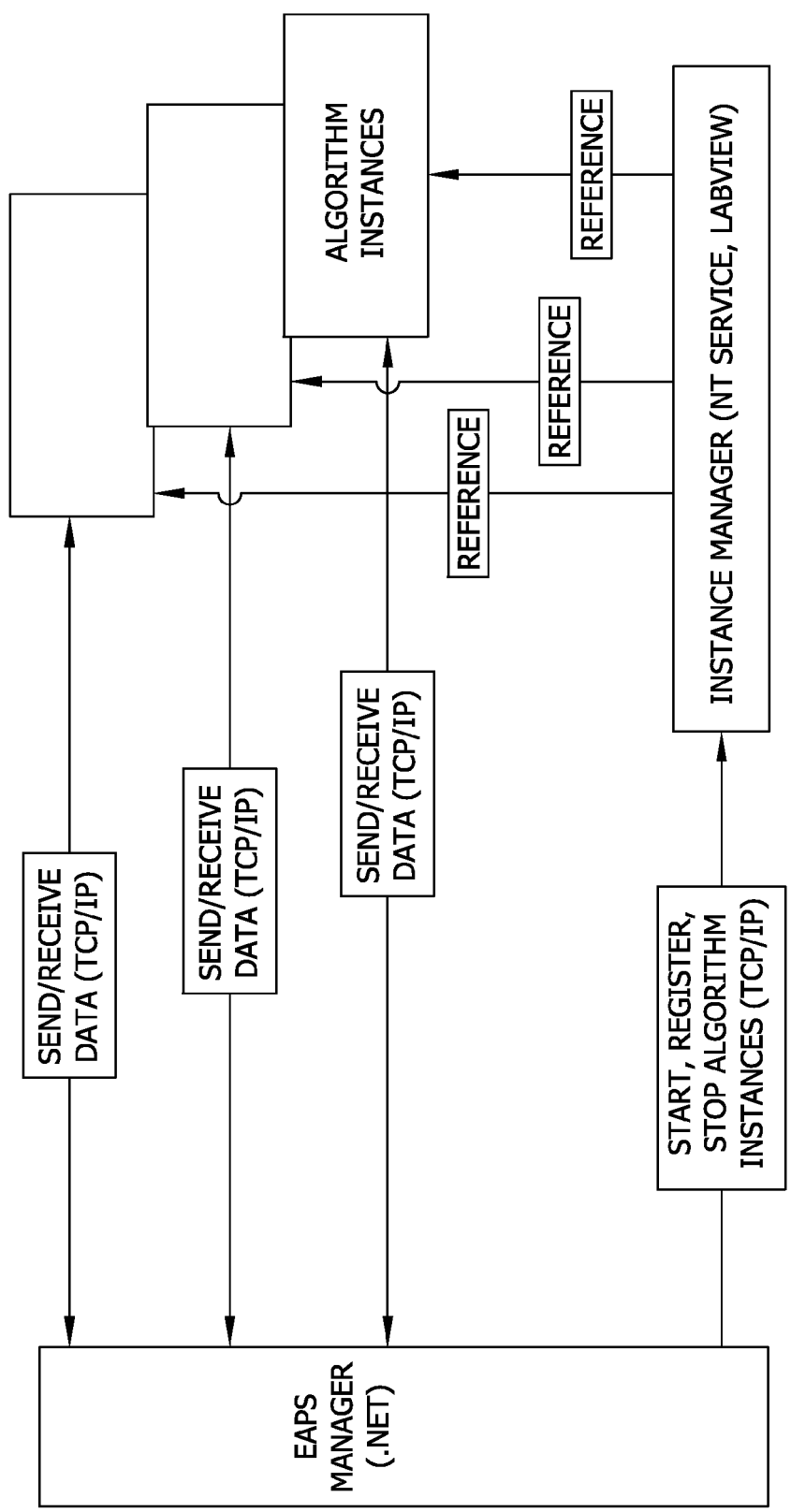
FIG. 3 is a block diagram of one embodiment of the EAPS (ECG Analysis and Processing Subsystem) architecture of the data center of FIG. 2.

FIG. 3 is a block diagram of one embodiment of the EAPS (ECG Analysis and Processing Subsystem) architecture of the data center of FIG. 2. In one embodiment, an algorithm subsystem for analyzing each data stream of each patient will be run on the EAPS servers within the data center. Algorithm instances will be run simultaneously, one for each data stream, by the EAPS. The EAPS, which will start each algorithm instance, provides all data for processing, and collects results of data processing. For example, the system would include a plurality of sensor devices 102 and a corresponding plurality of handheld devices 122. Each handheld device 122 would transmit a full disclosure ECG data packet signal 132 to the data center 142. The data center includes a plurality of algorithm instances for identifying anomalies in the ECG data and one instance is executed and applied to each full disclosure ECG data signal received by the data center.

When an algorithm instance processes full disclosure ECG data, it also changes its own internal state. This state is not carried over for the next full disclosure ECG packet, but rather stored and sent back to the EAPS. When new full disclosure ECG data arrives, the EAPS sends this state information back to the algorithm instance along with the full disclosure ECG data. The algorithm instance itself does not hold a state associated with the full disclosure ECG data.

Upon startup, each algorithm instance will receive a unique TCP/IP address and port number for communication with the EAPS. Then, this port number will be used for communication with this particular instance.

Figure 4:
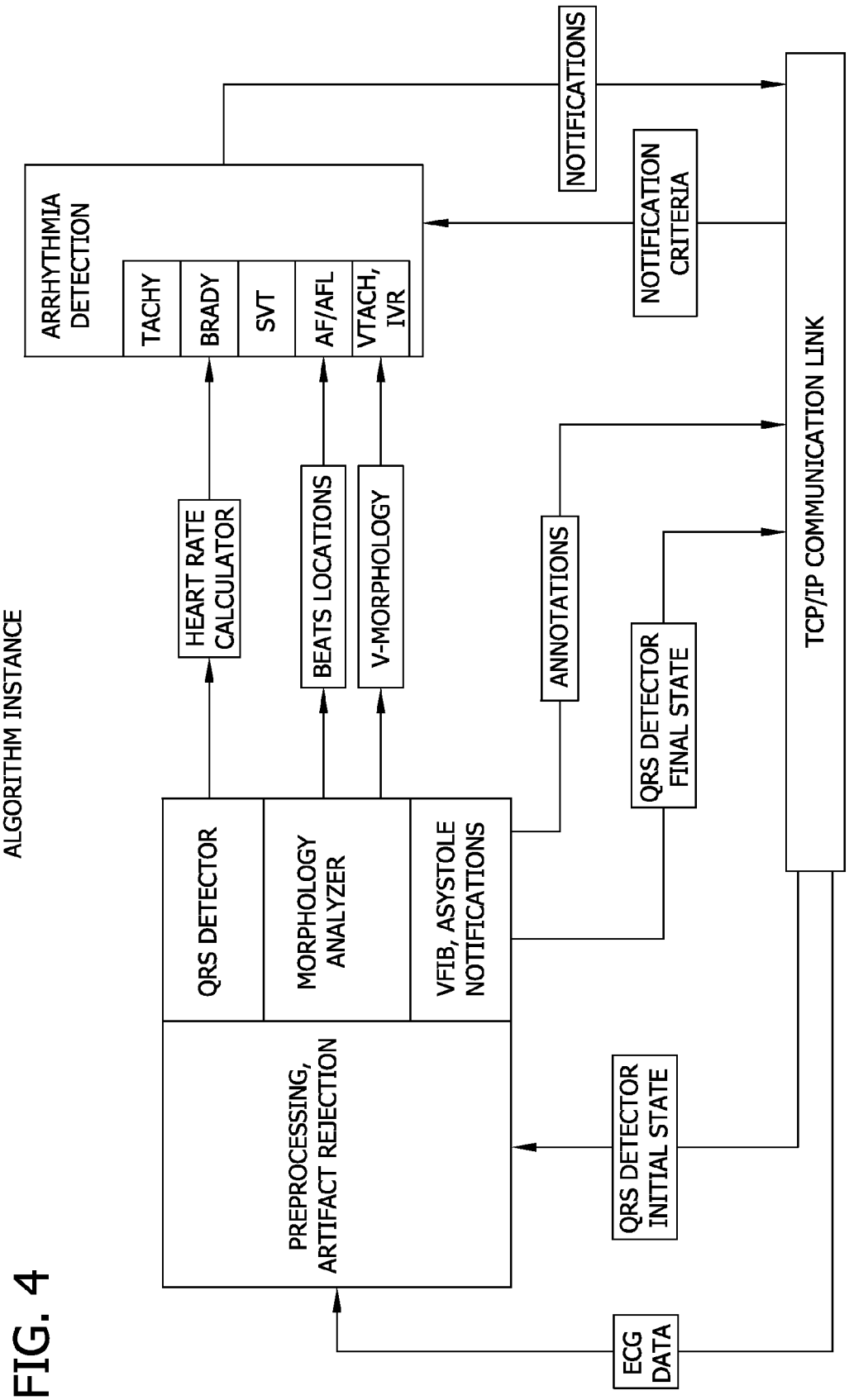
FIG. 4 is a block diagram of one embodiment of the algorithm instance of the data center.

FIG. 4 is a block diagram of one embodiment of the algorithm instance of the EAPS of the data center. Referring to FIGS. 3 and 4, each algorithm instance accepts full disclosure ECG data from a particular patient and returns annotations indicating areas of interest (portions or samples of the full disclosure data) to a technician. In one embodiment, the instance manager is a NT server and provides an interface for algorithm instances startup and registration with the EAPS manager, and algorithm instances shutdown. The instance manager keeps internal references for every algorithm instance. These references are used for instance startup and shutdown. The mechanism of interaction between instance manager and algorithm instances is native to the run-time environment (e.g., such as a Labview environment).

In one embodiment, each algorithm instance performs major tasks of processing the full disclosure ECG data including at least one of filtering (e.g., preprocessing, artifact rejection), QRS detection, morphology detection and analysis, ventricular fibrillation (VFIB) detection, asystole detection, heart-rate calculations, and/or rhythm detection (tachycardia, bradycardia, supraventricular tachycardia (SVT), atrial flutter (AF/AFL), ventricular tachycardia (V-tach) and idioventricular rhythm (IVR)). See FIG. 8, below.

As shown in FIG. 5, a ventricular fibrillation (VF) and/or SADA algorithm which may be executed by the sensor device, the handheld device, or the data center (independent of any QRS detector). The algorithm receives full disclosure ECG samples at 250 Hz and, after bandpass filtering, splits the data into two or more channels, each channel providing a high resolution full disclosure ECG acquisition signal (e.g., up to 1.25 microvolts per bit, 1000 Hz 16 bit samples per second, dynamic range of +/−40 mV, 0.05 to 150 Hz bandpass). Each channel is processed symmetrically with additional filtering either before or after the processing. The channels are combined and decision maker logic is applied to identify samples of arrhythmia. The logic of the ventricular fibrillation detection algorithm may be the same as the logic for the serious arrhythmia detection algorithm. However, the parameters of the VF detection algorithm are tuned to detect ventricular fibrillation only while the serious arrhythmia detection algorithm decision maker may also be configured to identify samples of high heart rate ECG e.g., ventricular tachycardia.

Regarding the sample marker system of FIG. 4, once the QRS detector processes the incoming full disclosure ECG data, the sample marker system looks for samples of arrhythmia contained in this full disclosure ECG packet using defined hard limits. Types of samples that are identified include those in the following table:

| Sample type | Limit (Default) | Limit Range |
| --- | --- | --- |
| Pause/Asystole | >3 seconds | 2-5 seconds |
| Bradycardia | <40 bpm | 20-50 bpm |
| Tachycardia | >180 bpm | 120-220 bpm |
| SVT | >30 sec | 5-60 sec |
| VT | Rate: >110 bpm (3 or more beats) | Rate: 80-150 bpm Beats: 3-10 |
| Idioventricular Rhythm | >30 beats | 5-50 beats |
| VF | Always | |
| AF | First onset for patient Then Vrate >150 or <40 BPM | 1-10 Onsets Vrate: 20-220 bpm |
| Patient Initiated | Always sent | |

Figure 6:
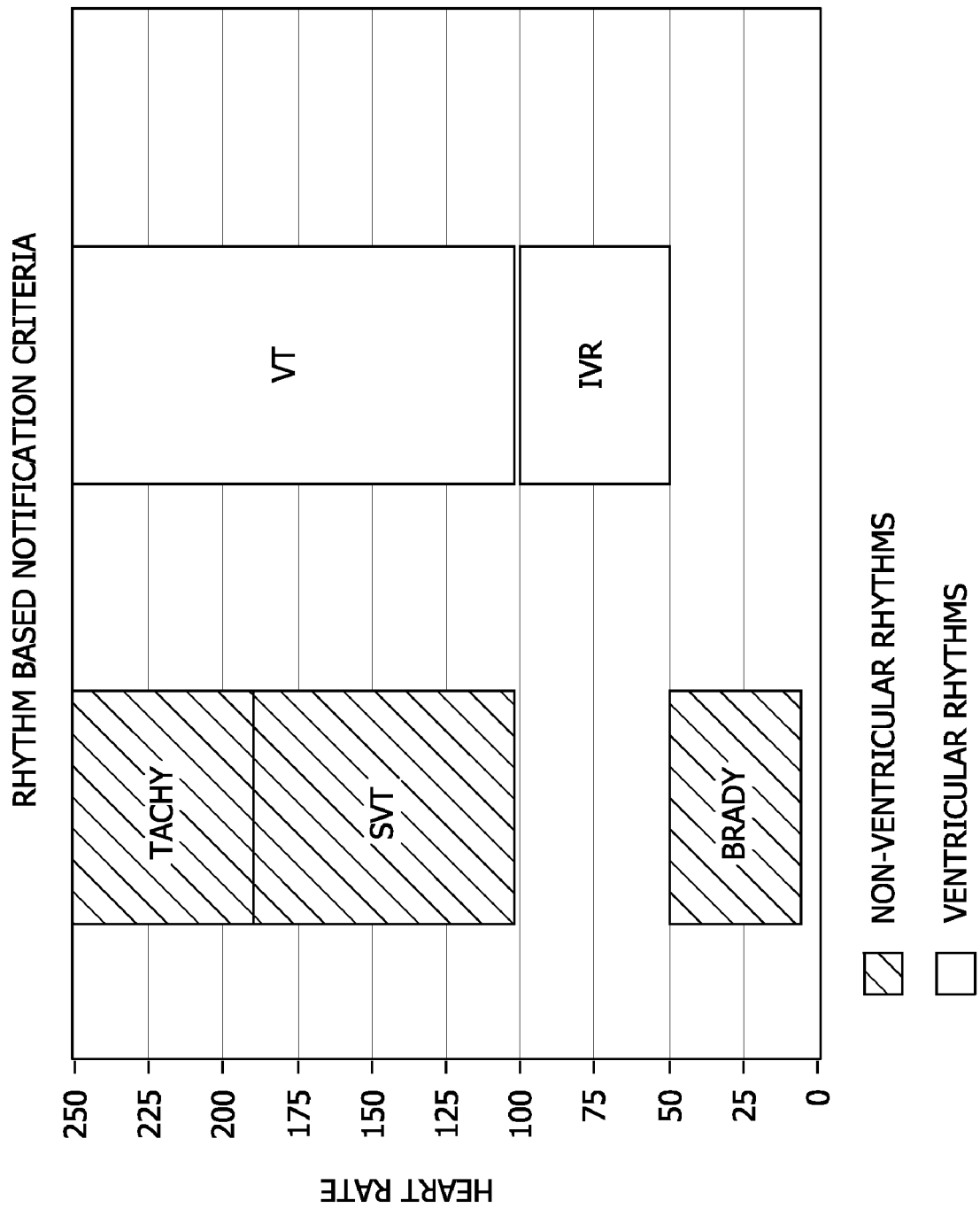
FIG. 6 is a graphical representation of rate- and rhythm based sample identification limits of the algorithm instance of the data center of FIG. 4.

Values of hard limits could be changed from defaults for any patient at any time. The algorithm is receiving hard limit values from the EAPS and generating sample markers according to received hard limits. A graphical representation of hard limit based sample identification is shown in FIG. 6. It is important to differentiate between "hard limit" and "soft limit" algorithms. SADA and what was formerly called the "representative event" algorithm are examples of soft limit algorithms. Soft limit algorithms include pre-defined thresholds which are not discrete whereas hard limit only include pre-defined thresholds.

A soft limit sample marker algorithm may be employed by the data center processor 146 for post-processing of patient's data. A soft limit algorithm can be used to identify samples when the hard limit detector does not detect any. These ECG samples are chosen in a way that would reflect the most serious of any particular samples that do not meet the hard limit criteria (e.g., lowest and highest heart rates for the day or night or longest pause). Soft limit samples types may be one or more of the following: tachycardia, bradycardia, and/or a pause.

Soft limit samples are generated for previously processed data: annotations are assumed to be available for the time interval of interest (usually, the last 24 hours). One form of an algorithm to soft limit samples is the following:

time interval of 10 minutes before the existing sample of the same type and 10 minutes after the existing sample is excluded from processing.

remaining data are analyzed for maximum severity and absence of artifacts, and based on this information, the best samples are marked from full disclosure ECG data and the corresponding soft limits samples are marked.

The severity of samples of arrhythmias is calculated accordingly to the sample type:

highest heart rate for a tachycardia sample type, lowest heart rate for a bradycardia sample type, and longest pause for a pause sample type.

It is important to note that soft limits samples do not have a predefined limit as a criterion for sample marking.

In operation, the system would be used as follows according to one example of one embodiment. The system would include a plurality of sensors 102 and a corresponding plurality of handheld devices 122, all simultaneously transmitting full disclosure ECG data packet signals via the cell network CN to the data center 142. The leads 112 would be attached to the patient who would be wearing the sensor device 102. If the leads fall off the patient or otherwise are not detecting ECG data, the sensor device 102 would alert the patient and send an alert to a technician via the data center. The patient would carry the handheld device 122 and install a modem at the patient's location for back-up connectivity. In the event that the sensor 102 is out of range of the handheld device 122, such as if the patient forgets to carry the handheld device 122, no data is lost because the sensor stores all data. The sensor may alert the patient that the sensor is out of range of the handheld device. In the event that the handheld device is not communicating with the data center via the cell network, the handheld device would attempt to communicate via the modem. If communication with the data center is not available, no data is lost because the sensor stores all data.

In one embodiment, the system may be configured for use by a patient having access to a cellular network for monitoring patient parameters other than ECG data. For example, the system would comprise the body sensor device adapted to be worn by the patient and having a sensor circuit detecting a full disclosure analog signal of a parameter indicative of a body function of the patient. The sensor processor stores full disclosure data corresponding to the detected analog signal in the sensor storage memory, and the sensor transmitter transmits a full disclosure signal including the full disclosure data stored in the sensor storage memory. Similarly, the handheld receiver receives the full disclosure signal, the handheld processor stores the full disclosure data included in the received full disclosure signal in the handheld storage memory, and the handheld transmitter transmits a packet signal including the full disclosure data stored in the handheld storage memory via the cellular network. The data center receiver receives the packet signal, the data center processor stores the full disclosure data included in the received packet signal in the data center storage memory, and the data center processor analyzes the full disclosure data stored in the data center storage memory to identify any parameter anomalies in the full disclosure data stored in the data center storage memory. The monitoring center permits the technician/physician device to evaluate the full disclosure data stored in the data center storage memory, for considering any identified parameter anomalies and for providing reports. As a result, the system has the ability to telemeter full disclosure parameter data from remote locations. As a specific example, modalities of the system may include monitoring parameters which indicate one or more of the following:
a sensor circuit detecting a full disclosure analog ECG signal indicative of the heart of the patient;
a sensor circuit detecting a full disclosure analog blood pressure signal indicative of the blood pressure of the patient;
a sensor circuit detecting a full disclosure analog body temperature signal indicative of the body temperature of the patient;
a sensor circuit detecting a full disclosure analog uterine contraction signal indicative of the contractions of the uterine of the patient;
a sensor circuit detecting a full disclosure analog signal indicative of the level (e.g., pulse oxygen) of the patient.

In one embodiment, several parameters, such as ECG and blood pressure data, may be simultaneously sensed, transmitted and analyzed by the system.

In one embodiment, it is contemplated that the sensor device 102 could be used as a stand-alone device as a holter recorder. In this embodiment, the sensor device 102 would include a USB or similar port or BT functionality to connect to a personal computer for downloading the holter data.

Having described the invention in detail, it will be apparent that modifications and variations are possible without departing from the scope of the invention defined in the appended claims.

For purposes of illustration, programs and other executable program components, such as the operating system, are illustrated herein as discrete blocks. It is recognized, however, that such programs and components reside at various times in different storage components of the computer, and are executed by the data processor(s) of the computer.

Although described in connection with an exemplary computing system environment, embodiments of the invention are operational with numerous other general purpose or special purpose computing system environments or configurations. The computing system environment is not intended to suggest any limitation as to the scope of use or functionality of any aspect of the invention. Moreover, the computing system environment should not be interpreted as having any dependency or requirement relating to any one or combination of components illustrated in the exemplary operating environment. Examples of well known computing systems, environments, and/or configurations that may be suitable for use with aspects of the invention include, but are not limited to, personal computers, server computers, hand-held or laptop devices, multiprocessor systems, microprocessor-based systems, set top boxes, programmable consumer electronics, mobile telephones, network PCs, minicomputers, mainframe computers, distributed computing environments that include any of the above systems or devices, and the like.

Embodiments of the invention may be described in the general context of computer-executable instructions, such as program modules, executed by one or more computers or other devices. Generally, program modules include, but are not limited to, routines, programs, objects, components, and data structures that perform particular tasks or implement particular abstract data types. Aspects of the invention may also be practiced in distributed computing environments where tasks are performed by remote processing devices that are linked through a communications network. In a distributed computing environment, program modules may be located in both local and remote computer storage media including memory storage devices.

In operation, computers and/or servers may execute the computer-executable instructions such as those illustrated herein to implement aspects of the invention.

The order of execution or performance of the operations in embodiments of the invention illustrated and described herein is not essential, unless otherwise specified. That is, the operations may be performed in any order, unless otherwise specified, and embodiments of the invention may include additional or fewer operations than those disclosed herein. For example, it is contemplated that executing or performing a particular operation before, contemporaneously with, or after another operation is within the scope of aspects of the invention.

Embodiments of the invention may be implemented with computer-executable instructions. The computer-executable instructions may be organized into one or more computer-executable components or modules on a tangible computer readable storage medium. Aspects of the invention may be implemented with any number and organization of such components or modules. For example, aspects of the invention are not limited to the specific computer-executable instructions or the specific components or modules illustrated in the figures and described herein. Other embodiments of the invention may include different computer-executable instructions or components having more or less functionality than illustrated and described herein.

When introducing elements of aspects of the invention or the embodiments thereof, the articles "a," "an," "the," and "said" are intended to mean that there are one or more of the elements. The terms "comprising," "including," and "having" are intended to be inclusive and mean that there may be additional elements other than the listed elements.

In view of the above, it will be seen that several advantages of the invention are achieved and other advantageous results attained.

Having described aspects of the invention in detail, it will be apparent that modifications and variations are possible without departing from the scope of aspects of the invention as defined in the appended claims. As various changes could be made in the above constructions, products, and methods without departing from the scope of aspects of the invention, it is intended that all matter contained in the above description and shown in the accompanying drawings shall be interpreted as illustrative and not in a limiting sense.

What is claimed is:

1. A system for use by a patient having access to a cellular network comprising:
    a body sensor device adapted to be worn by the patient and having a sensor circuit, a sensor processor, a sensor storage memory and a sensor transmitter, wherein the sensor circuit detects an analog full disclosure ECG signal of the patient, wherein the sensor processor stores full disclosure ECG data corresponding to the detected analog signal in the sensor storage memory, and wherein the sensor transmitter transmits a full disclosure ECG signal including the full disclosure ECG data stored in the sensor storage memory;
    a handheld device adapted to be carried by the patient and having a handheld storage memory, a handheld processor, a handheld receiver and a handheld transmitter, wherein the handheld receiver receives the full disclosure ECG signal, wherein the handheld processor stores the full disclosure ECG data included in the received full disclosure ECG signal in the handheld storage memory, and wherein the handheld transmitter transmits a packet signal including the full disclosure ECG data stored in the handheld storage memory via the cellular network;
    a data center remote from the patient and having a data center receiver, a data center processor and a data center storage memory, wherein the data center receiver receives the packet signal, wherein the data center processor stores the full disclosure ECG data included in the received packet signal in the data center storage memory, and wherein the data center processor analyzes the full disclosure ECG data stored in the data center storage memory to identify any anomalies in the full disclosure ECG data stored in the data center storage memory;
    a monitoring center linked to the data center and having a technician port accessible by a technician device for evaluating the full disclosure ECG data stored in the data center storage memory, for considering any identified anomalies and for providing reports, and a physician port accessible by a physician for viewing provided technician reports and for viewing the full disclosure ECG data stored in the data center storage memory,
    whereby the system has the ability to telemeter full disclosure ECG data from remote locations.

2. The system of claim 1 wherein the sensor transmitter streams the full disclosure ECG signal including the full disclosure ECG data in near real-time almost immediately after the detected full disclosure ECG data is stored in the sensor storage memory, wherein the handheld transmitter streams the packet signal including the full disclosure ECG data almost immediately after the full disclosure ECG data is stored in the handheld storage memory and wherein the data center streams the full disclosure ECG data included in the received packet signal to the technician port for near real-time viewing by the technician and/or wherein the data center streams the full disclosure ECG data included in the received packet signal to the physician port for near real-time viewing by the physician.

3. The system of claim 1 wherein the data center presents the technician or physician with an option to view full disclosure ECG data which is previous to and/or subsequent to the full disclosure data being viewed.

4. The system of claim 1 wherein the data center processes the full disclosure ECG data from multiple patients simultaneously.

5. The system of claim 1 further comprising two way communication between the handheld device and the data center and between the data center and the monitoring center such that the system has the ability to transmit to a transducer of the handheld device a voice instruction to the patient from the technician via the monitoring center and/or from the physician via the monitoring center to meet a particular clinical need.

6. The system of claim 1 wherein the full disclosure ECG signal acquired by the body sensor device comprises at least 2 channels of data from the sensor, each channel providing a high resolution full disclosure ECG acquisition signal.

7. The system of claim 1 wherein the full disclosure ECG signal acquired by the body sensor device comprises at least 2 channels, each providing a dynamic range of +/−40 mV.

8. The system of claim 1 wherein the data center incorporates a muscle artifact rejection algorithm for noise rejection.

9. The system of claim 1 wherein the handheld device comprises an integrated application and baseband processor in a pre-certified module.

10. The system of claim 1 wherein the handheld device accesses a WAN and includes at least one of:
    Graduated back off and PDP context re-connect algorithms;
    Use of adaptive full disclosure ECG resolution to reduce data payload;
    Use of lossless compression to reduce data payload; and
    Ability to connect to a home based POTS modem with a class 1 BT Radio incorporated in the handheld device.

11. The system of claim 1 further comprising a modem connected to the data center via the Internet or a phone line, wherein the handheld transmitter transmits a second signal including the full disclosure ECG data to the modem when the handheld is not communicating with the cellular network and wherein said modem has a receiver for receiving the second signal including the full disclosure ECG data and a transmitter for transmitting the full disclosure ECG data to the data center via the Internet or the phone line.

12. The system of claim 1 wherein the handheld transmitter transmits the packet signal with low latency.

13. The system of claim 1 wherein the body sensor device is battery powered, wherein the handheld device is battery powered, wherein the body sensor device transmits to the handheld device information indicative of its battery level, and wherein the handheld device includes a display for displaying the battery levels of both the body sensor device and the handheld device.

14. The system of claim 1 wherein the body sensor device and/or the handheld storage memory comprises at least 30 days of full disclosure full disclosure ECG data storage.

15. The system of claim 1 wherein the body sensor device and the handheld device communicate via a low power local RF link protocol for power saving.

16. The system of claim 1 wherein the sensor processor includes a serious arrhythmia detection algorithm (SADA) which is executed by the processor, said SADA program analyzing at a low resolution in near real-time the full disclosure ECG data stored in its memory to detect any predefined arrhythmia events when the sensor device and the handheld device are not communicating or when the handheld device is not communicating with the cellular network, and wherein the SADA program provides an alert to the patient when one or more events is detected.

17. The system of claim 1 wherein the data center processor provides a full disclosure navigable waveform that provides drill down access to portions of a particular day's full disclosure ECG data by presenting a secondary measure such as HR or noise level of the full disclosure ECG data.

18. The system of claim 1 wherein the data center permits the technician and/or the physician to view the stored full disclosure ECG data in low resolution and to drill down selected full disclosure ECG data at a higher resolution.

19. The system of claim 1 wherein the data center permits the technician and/or the physician to view the stored full disclosure ECG data of a particular period of time and to view related ECG data before or after the particular period of time.

20. The system of claim 1 further comprising a plurality of sensor devices and a corresponding plurality of handheld devices, each handheld device transmitting a full disclosure ECG data signal to the data center, wherein the data center includes a plurality of algorithm instances for identifying anomalies in the ECG data and wherein one instance is executed and applied to each full disclosure ECG data signal received by the data center.

21. A system for use by a patient having access to a cellular network, said system comprising:
- a body sensor device adapted to be worn by the patient and having a sensor circuit, a sensor processor, a sensor storage memory and a sensor transmitter, wherein the sensor circuit detects a full disclosure analog signal of a parameter indicative of a body function of the patient, wherein the sensor processor stores full disclosure data corresponding to the detected analog signal in the sensor storage memory, and wherein the sensor transmitter transmits a full disclosure signal including the full disclosure data stored in the sensor storage memory;
- a handheld device adapted to be carried by the patient and having a handheld storage memory, a handheld processor, a handheld receiver and a handheld transmitter, wherein the handheld receiver receives the full disclosure signal, wherein the handheld processor stores the full disclosure data included in the received full disclosure signal in the handheld storage memory, and wherein the handheld transmitter transmits a packet signal including the full disclosure data stored in the handheld storage memory via the cellular network;
- a data center remote from the patient and having a data center receiver, a data center processor and a data center storage memory, wherein the data center receiver receives the packet signal, wherein the data center processor stores the full disclosure data included in the received packet signal in the data center storage memory, and wherein the data center processor analyzes the full disclosure data stored in the data center storage memory to identify any parameter anomalies in the full disclosure data stored in the data center storage memory;
- a monitoring center linked to the data center and having a technician port accessible by a technician device for evaluating the full disclosure data stored in the data center storage memory, for considering any identified anomalies and for providing reports, and a physician port accessible by a physician for viewing provided technician reports and for viewing the full disclosure data stored in the data center storage memory, whereby the system has the ability to telemeter full disclosure parameter data from remote locations.

22. The system of claim 21 wherein the sensor comprises at least one of:
- a sensor circuit detecting a full disclosure analog ECG signal indicative of the heart of the patient;
- a sensor circuit detecting a full disclosure analog blood pressure signal indicative of the blood pressure of the patient;
- a sensor circuit detecting a full disclosure analog body temperature signal indicative of the body temperature of the patient;
- a sensor circuit detecting a full disclosure analog uterine contraction signal indicative of the contractions of the uterine of the patient;
- a sensor circuit detecting a full disclosure analog signal indicative of the level of the patient.

* * * * *